United States Patent
Pathak et al.

(10) Patent No.: US 11,648,063 B2
(45) Date of Patent: May 16, 2023

(54) SYSTEMS AND METHODS FOR ELECTRODE ORIENTATION DETERMINATION IN DEEP BRAIN STIMULATION (DBS)

(71) Applicant: Advanced Neuromodulation Systems, Inc., Plano, TX (US)

(72) Inventors: Yagna Pathak, Skokie, IL (US); Hyun-Joo Park, Frisco, TX (US); Simeng Zhang, Frisco, TX (US); Anahita Kyani, Plano, TX (US); Erika Ross, Dallas, TX (US); Dehan Zhu, Plano, TX (US); Douglas Lautner, Frisco, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 221 days.

(21) Appl. No.: 17/113,385

(22) Filed: Dec. 7, 2020

(65) Prior Publication Data
US 2022/0175458 A1 Jun. 9, 2022

(51) Int. Cl.
*A61B 8/00* (2006.01)
*A61B 34/20* (2016.01)
(Continued)

(52) U.S. Cl.
CPC ............ *A61B 34/20* (2016.02); *A61N 1/0534* (2013.01); *G06K 9/6257* (2013.01); *G06T 7/73* (2017.01); *G06V 10/40* (2022.01); *G16H 20/40* (2018.01); *G16H 30/40* (2018.01); *G16H 50/20* (2018.01); *A61B 2034/2065* (2016.02); *A61B 2090/374* (2016.02); *A61B 2090/3762* (2016.02); *G06T 2207/10064* (2013.01); *G06T 2207/10081* (2013.01); *G06T 2207/10088* (2013.01); *G06T 2207/20021* (2013.01); *G06T 2207/20081* (2013.01); *G06T 2207/20084* (2013.01);
(Continued)

(58) Field of Classification Search
CPC combination set(s) only.
See application file for complete search history.

(56) References Cited

U.S. PATENT DOCUMENTS 10,543,361 B2   1/2020   Ramani et al.
11,318,297 B2   5/2022   Li et al.
(Continued)

*Primary Examiner* — Joel F Brutus
(74) *Attorney, Agent, or Firm* — Armstrong Teasdale LLP

(57) ABSTRACT

The present disclosure provides systems and methods for estimating an orientation of an implanted deep brain stimulation (DBS) lead. Such methods include generating an initial image dataset, down-sampling a respective image or adding noise to images of the subset of the initial image dataset, and re-slicing at least a subset of the modified image dataset along an alternative primary imaging axis, to generate an integrated image dataset. The method also include partitioning the integrated image dataset into a preliminary training image dataset and a testing image dataset, and re-sizing at least a subset of the preliminary training image dataset with a localized field of view around a depicted DBS lead, to generate a training image dataset. The method further includes training a machine-learning model using the training image dataset, and executing the trained machine-learning model to estimate, during a DBS implantation procedure, an orientation of a subject implanted DBS lead.

21 Claims, 7 Drawing Sheets

(51) Int. Cl.
  *G06K 9/62* (2022.01)
  *G06T 7/73* (2017.01)
  *A61N 1/05* (2006.01)
  *G16H 30/40* (2018.01)
  *G16H 20/40* (2018.01)
  *G16H 50/20* (2018.01)
  *G06V 10/40* (2022.01)
  *A61B 90/00* (2016.01)

(52) U.S. Cl.
  CPC .............. *G06T 2207/30016* (2013.01); *G06V 2201/031* (2022.01)

(56) References Cited

U.S. PATENT DOCUMENTS

| | | | |
|---|---|---|---|
| 2009/0198306 A1* | 8/2009 | Goetz | A61N 1/37264 600/407 |
| 2019/0321106 A1* | 10/2019 | Bergman | A61N 1/0551 |
| 2019/0366074 A1 | 12/2019 | Carlton et al. | |
| 2022/0061784 A1 | 3/2022 | Baxter et al. | |

\* cited by examiner

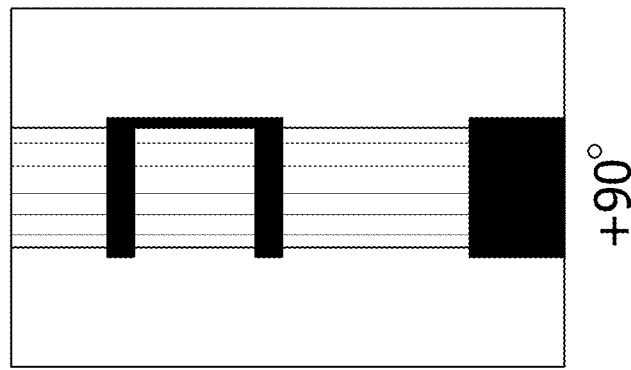
FIG. 5C +90°
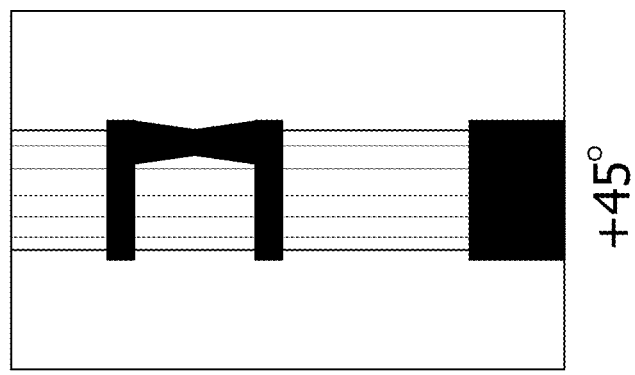
FIG. 5B +45°
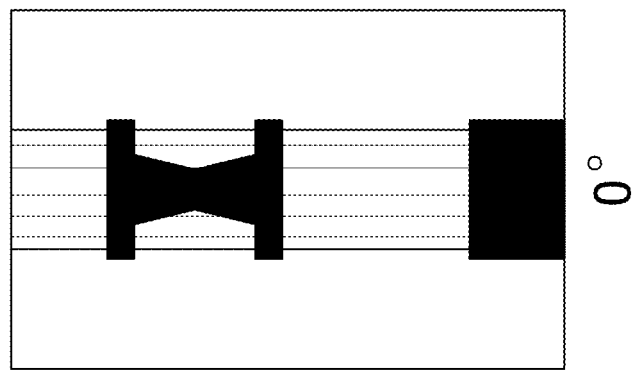
FIG. 5A 0°

SYSTEMS AND METHODS FOR ELECTRODE ORIENTATION DETERMINATION IN DEEP BRAIN STIMULATION (DBS)

BACKGROUND OF THE DISCLOSURE

A. Field of the Disclosure

The present disclosure relates generally to neurostimulation systems, and, more particularly, to determining implanted electrode orientation in neurostimulation systems.

B. Background Art

Deep brain stimulation (DBS) is an established neuromodulation therapy for the treatment of movement disorders, and has been shown to improve cardinal motor symptoms of Parkinson's Disease (PD), such as bradykinesia, rigidity, and tremors. DBS is also used to essential tremor (ET). DBS is performed by placing a neurostimulator including a lead with embedded electrodes into the patient's brain, and selectively activating the electrodes to send electrical pulses to specific target tissues in the brain.

The success of DBS therapy is highly dependent upon correct placement of the neurostimulator, including both the location and orientation of the electrodes, to ensure stimulation of the desired target tissues. Typically, placement of the DBS lead is informed by micro-electrode recordings and can be time consuming for the physician and burdensome for the patient. Additionally, brain shift due to cerebrospinal fluid (CSF) leakage during surgery may contribute to uncertainty regarding final lead position. Various imaging methods, such as fluoroscopy and CT imaging, are used intra-operatively and post-operatively, to attempt to more precisely identify or confirm the location of the lead. However, none of these imaging techniques enables full identification or confirmation of the lead placement, including precise location and orientation of electrodes. Fluoroscopy imaging enables identification of lead rotation in two dimensions, but not the precise location due to a lack of depth information. In contrast, CT imaging includes depth information but lacks the appropriate resolution to detect orientation. Additionally, clinical-level CT imaging, which prioritizes scanning time, to the detriment of image quality, is vulnerable to artifacts that make interpretation of CT imaging difficult.

One known attempted solution for the deficiencies of conventional imaging techniques is an algorithm that leverages shadow patterns in CT imaging to approximate an orientation of the lead. However, this algorithm suffers from high levels of variance—up to 30° to 45° of variance—that limits its clinical utility. The variance increases further as CT image quality degrades.

BRIEF SUMMARY OF THE DISCLOSURE

In one embodiment, the present disclosure is directed to a computing device for estimating an orientation of an implanted deep brain stimulation (DBS) lead. The computing device includes a processor, and a memory device communicatively coupled to the processor. The memory device includes instructions that, when executed, cause the processor to: (i) generate an initial image dataset from a plurality of clinical images and a plurality of phantom images, each image in the initial image dataset including a depiction of an implanted DBS lead and a label of an orientation of the implanted DBS lead; (ii) modify the initial image dataset by duplicating and modifying at least a subset of the initial image dataset, the modifying including at least one of down-sampling a respective image or adding noise to a respective image of the subset of the initial image dataset, to generate a modified image dataset; (iii) modify the modified image dataset by duplicating and re-slicing at least a subset of the modified image dataset, the re-slicing including re-slicing a respective image along an alternative primary imaging axis, to generate an integrated image dataset; (iv) partition the integrated image dataset into a preliminary training image dataset and a testing image dataset; (v) modify the preliminary training image dataset by duplicating and re-sizing at least a subset of the preliminary training image dataset with a localized field of view around the respective depiction of the implanted DBS lead, to generate a training image dataset; (vi) train a machine-learning model using the training image dataset, including training the machine-learning model to associate one or more image artifacts with the orientation of the implanted DBS lead; and (vii) execute the trained machine-learning model to estimate, during a DBS implantation procedure, an orientation of a subject implanted DBS lead.

In another embodiment, the present disclosure is directed to a computer-implemented method for estimating deep brain stimulation (DBS) lead orientation. The method includes: (i) generating an initial image dataset from a plurality of clinical images and a plurality of phantom images, each image in the initial image dataset including a depiction of an implanted DBS lead and a label of an orientation of the implanted DBS lead; (ii) modifying the initial image dataset by duplicating and modifying at least a subset of the initial image dataset, the modifying including at least one of down-sampling a respective image or adding noise to a respective image of the subset of the initial image dataset, to generate a modified image dataset; (iii) modifying the modified image dataset by duplicating and re-slicing at least a subset of the modified image dataset, the re-slicing including re-slicing a respective image along an alternative primary imaging axis, to generate an integrated image dataset; (iv) partitioning the integrated image dataset into a preliminary training image dataset and a testing image dataset; (v) modifying the preliminary training image dataset by duplicating and re-sizing at least a subset of the preliminary training image dataset with a localized field of view around the respective depiction of the implanted DBS lead, to generate a training image dataset; (vi) training a machine-learning model using the training image dataset, including training the machine-learning model to associate one or more image artifacts with the orientation of the implanted DBS lead; and (vii) executing the trained machine-learning model to estimate, during a DBS implantation procedure, an orientation of a subject implanted DBS lead.

In yet another embodiment, the present disclosure is directed to non-transitory computer-readable media having computer-executable instructions thereon. When executed by a processor of a computing device communicatively coupled to a memory device, the computer-executable instructions cause the processor of the computing device to: (i) generate an initial image dataset from a plurality of clinical images and a plurality of phantom images, each image in the initial image dataset including a depiction of an implanted DBS lead and a label of an orientation of the implanted DBS lead; (ii) modify the initial image dataset by duplicating and modifying at least a subset of the initial image dataset, the modifying including at least one of down-sampling a respective image or adding noise to a respective image of the subset of the initial image dataset, to generate a modified image dataset; (iii) modify the modified image dataset by duplicating and re-slicing at least a subset of the modified image dataset, the re-slicing including re-slicing a respective image along an alternative primary imaging axis, to generate an integrated image dataset; (iv) partition the integrated image dataset into a preliminary training image dataset and a testing image dataset; (v) modify the preliminary training image dataset by duplicating and re-sizing at least a subset of the preliminary training image dataset with a localized field of view around the respective depiction of the implanted DBS lead, to generate a training image dataset; (vi) train a machine-learning model using the training image dataset, including training the machine-learning model to associate one or more image artifacts with the orientation of the implanted DBS lead; and (vii) execute the trained machine-learning model to estimate, during a DBS implantation procedure, an orientation of a subject implanted DBS lead.

The foregoing and other aspects, features, details, utilities and advantages of the present disclosure will be apparent from reading the following description and claims, and from reviewing the accompanying drawings.

BRIEF DESCRIPTION OF THE DRAWINGS

FIGS. 5A-5C depict representations of fluoroscopic images identifying DBS lead orientation.

Corresponding reference characters indicate corresponding parts throughout the several views of the drawings.

DETAILED DESCRIPTION OF THE DISCLOSURE

Figure 1:
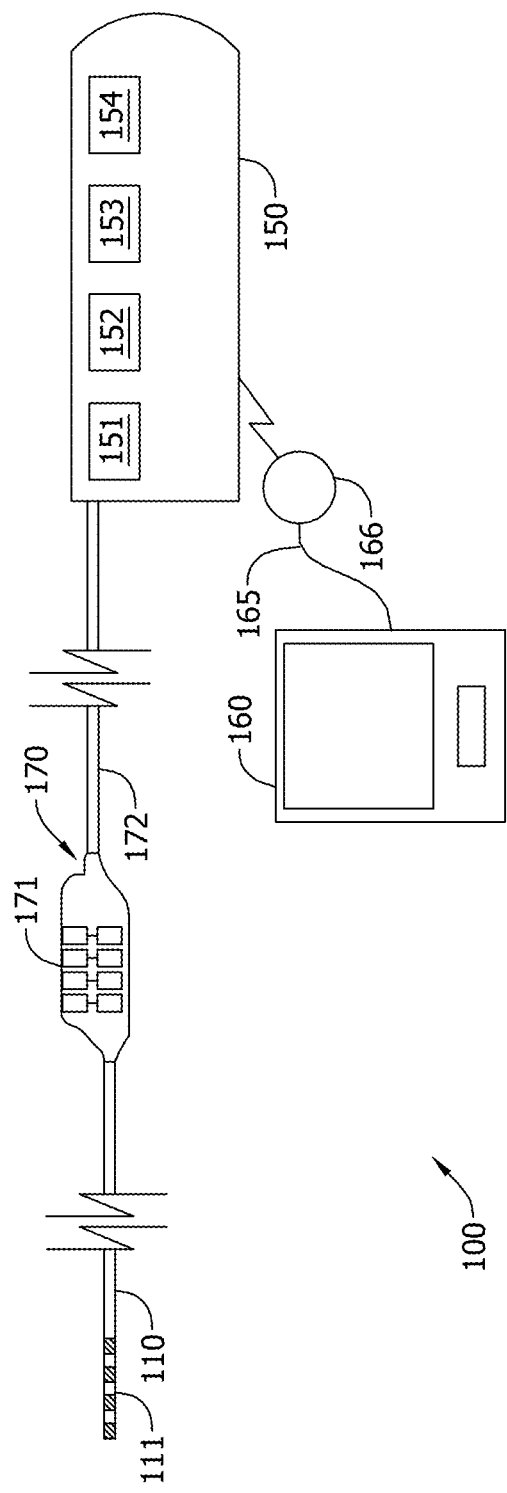
FIG. 1 is a schematic view of one embodiment of a stimulation system.

The present disclosure provides systems and methods for estimating an orientation of an implanted deep brain stimulation (DBS) lead, specifically during an implantation procedure. A computing device trains a machine-learning model using a set of training images that includes images depicting implanted DBS leads and labels of the orientation of the implanted DBS leads. The computing device processes the training set of images to associate image features of the training set of images with the labelled orientation. The trained machine-learning model receives a subject image of a subject implanted DBS lead with an unknown orientation and outputs an estimation of the orientation of the subject implanted DBS lead.

As used herein, "location" of an implanted DBS lead refers generally to a depth of the DBS lead or its relative location along a z-axis taken longitudinally through a patient's body. "Location" may additional refer to the location of the implanted DBS lead within an imaging plane (e.g., a horizontal x-y plane, orthogonal to the z-axis, taken through a patient's head). "Orientation" of a DBS lead may refer to a rotational orientation that can be defined in a three-axis coordinate system (x-y-z/yaw-pitch-roll) or based on a major or longitudinal axis of the DBS lead. The latter approach may include information about the 3-axes to be sufficiently usable. An origin angle in the three-axis coordinate system may also be defined based on coordinate context. For example, zero degrees would imply that the DBS lead was placed orthogonal to an axial plane and parallel to the sagittal and coronal planes, and an orientation marker thereof, as described further herein, was facing true anterior (e.g., towards the nose).

Neurostimulation systems generally include a pulse generator and one or more leads. A stimulation lead includes a lead body of insulative material that encloses electrical conductors, or wires. The distal end of the stimulation lead includes multiple electrodes, or contacts, that are electrically coupled to the electrical conductors. The proximal end of the lead body includes multiple terminals (also electrically coupled to the electrical conductors) adapted to receive electrical pulses. In DBS systems, the stimulation lead is implanted within the brain tissue to deliver the electrical pulses. The stimulation leads are then tunneled to another location within the patient's body to be electrically connected with a pulse generator or, alternatively, to an "extension." The pulse generator is typically implanted within a subcutaneous pocket created during the implantation procedure.

The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

Referring now to the drawings, and in particular to FIG. 1, a stimulation system is indicated generally at 100. Stimulation system 100 generates electrical pulses for application to tissue of a patient, or subject, according to one embodiment. System 100 includes an implantable pulse generator (IPG) 150 that is adapted to generate electrical pulses for application to tissue of a patient. IPG 150 typically includes a metallic housing that encloses a controller 151, pulse generating circuitry 152, a battery 153, far-field or near-field communication circuitry 154, and other appropriate circuitry and components of the device. Controller 151 typically includes a microcontroller or other suitable processor for controlling the various other components of the device. Software code is typically stored in memory of IPG 150 for execution by the microcontroller or processor to control the various components of the device.

IPG 150 may comprise one or more attached extension components 170 or be connected to one or more separate extension components 170. Alternatively, one or more stimulation leads 110 may be connected directly to IPG 150. Within IPG 150, electrical pulses are generated by pulse generating circuitry 152 and are provided to switching circuitry. The switching circuit connects to output wires, traces, lines, or the like (not shown) that are electrically coupled to internal electrical conductors (not shown) of a lead body 172 of extension component 170. The electrical conductors, or wires, are electrically coupled to electrical connectors (e.g., "Bal-Seal" connectors) within a connector portion 171 of extension component 170. The terminals of one or more stimulation leads 110 are inserted within connector portion 171 for electrical connection with respective connectors. Thereby, the pulses originating from IPG 150 and conducted through the conductors of lead body 172 are provided to stimulation lead 110. The pulses are then conducted through the conductors of lead 110 and applied to tissue of a patient via electrodes 111. Any suitable known or later developed design may be employed for connector portion 171.

For implementation of the components within IPG 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within IPG 150. Different pulses on different electrodes may be generated using a single set of pulse generating circuitry using consecutively generated pulses according to a "multi-stim set program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may include a lead body of electrically insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number and type of electrodes 111, terminals, and internal conductors.

An external controller device 160 permits the operations of IPG 150 to be controlled by user after IPG 150 is implanted within a patient. Controller device 160 can be implemented by utilizing a suitable handheld processor-based system that possesses wireless communication capabilities. Software is typically stored in memory of controller device 160 to control the various operations of controller device 160, including stimulation operations and operations for charging IPG 150. For example, to charge IPG 150, a "wand" 165 including a coil 166 may be electrically connected to controller device 160. The patient places the primary coil 166 against the patient's body immediately above a secondary coil (not shown), i.e., a coil of the implantable medical device. Controller device 160 generates an AC-signal to drive current through coil 166 of wand 165. The current induced in the coil of the implantable pulse generator is rectified and regulated to recharge battery of IPG 150. The charging circuitry may also communicate status messages to controller device 160 during charging operations using pulse-loading or any other suitable technique. For example, controller device 160 may communicate the coupling status, charging status, charge completion status, etc.

Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 150.

Controller device 160 preferably provides one or more user interfaces to allow the user to operate IPG 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stim set during execution of program), etc. In the methods and systems described herein, parameters may include, for example, a number of pulses in a burst (e.g., 3, 4, or 5 pulses per burst), an intra-burst frequency (e.g., 130 Hz), an inter-burst frequency (e.g., 3-20 Hz), and a delay between a first and second burst.

IPG 150 modifies its internal parameters in response to the control signals from controller device 160 to vary the stimulation characteristics of stimulation pulses transmitted through stimulation lead 110 to the tissue of the patient. Neurostimulation systems, stim sets, and multi-stim set programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference. Example commercially available neurostimulation systems include the EON MINI™ pulse generator and RAPID PROGRAMMER™ device from Abbott Laboratories.

The systems and methods described herein enable identifying, or estimating, the location and/or orientation of stimulation lead 110 to improve therapeutic outcomes. That is, by improving accuracy in the estimated location of DBS lead 110 within the patient's tissue, the stimulation pulses may be more precisely directed to the target tissue. Moreover, the overall procedure time may be significantly reduced, by reducing or eliminating the "trial and error" methods conventionally undertaken by the physician to locate and orient stimulation lead 110.

Figure 2:
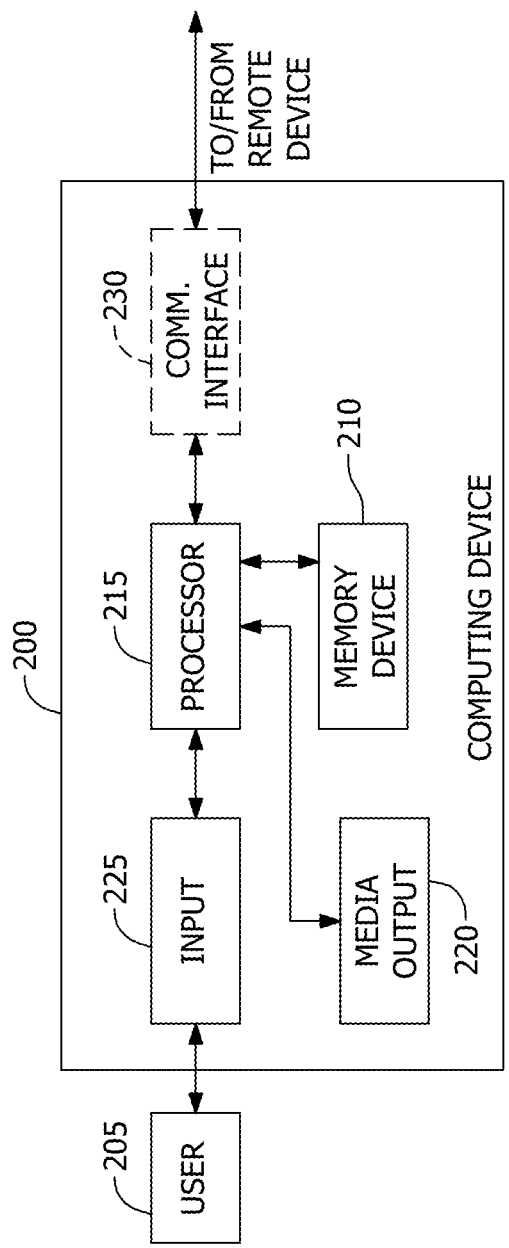
FIG. 2 is a block diagram of one embodiment of a computing device that may be used to determine an orientation of lead electrodes.

FIG. 2 is a block diagram of one embodiment of a computing device 200 that may be used to estimate the orientation of an implanted DBS lead (e.g., stimulation lead 110) using minimal input image data (e.g., a single input image, such as a clinical-level CT image), as described further herein. Computing device 200 may include any suitable computing device, including a computing device operable in a clinical setting (e.g., as part of a DBS lead implantation procedure). In some embodiments, computing device 200 is operated, at least in part, by a user 205, such as a clinician, physician, or other clinical entity.

In this embodiment, computing device 200 includes at least one memory device 210 and a processor 215 coupled to memory device 210 for executing instructions. In some embodiments, executable instructions are stored in memory device 210. In the illustrated embodiment, computing device 200 performs one or more operations described herein by programming processor 215. For example, processor 215 may be programmed by encoding an operation as one or more executable instructions and by providing the executable instructions in memory device 210. Memory device 210 is also configured to store additional and/or alternative data, including, for example, image data.

Processor 215 may include one or more processing units (e.g., in a multi-core configuration). Further, processor 215 may be implemented using one or more heterogeneous processor systems in which a main processor is present with secondary processors on a single chip. In another illustrative example, processor 215 may be a symmetric multi-processor system containing multiple processors of the same type. Further, processor 215 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein.

Figure 3:
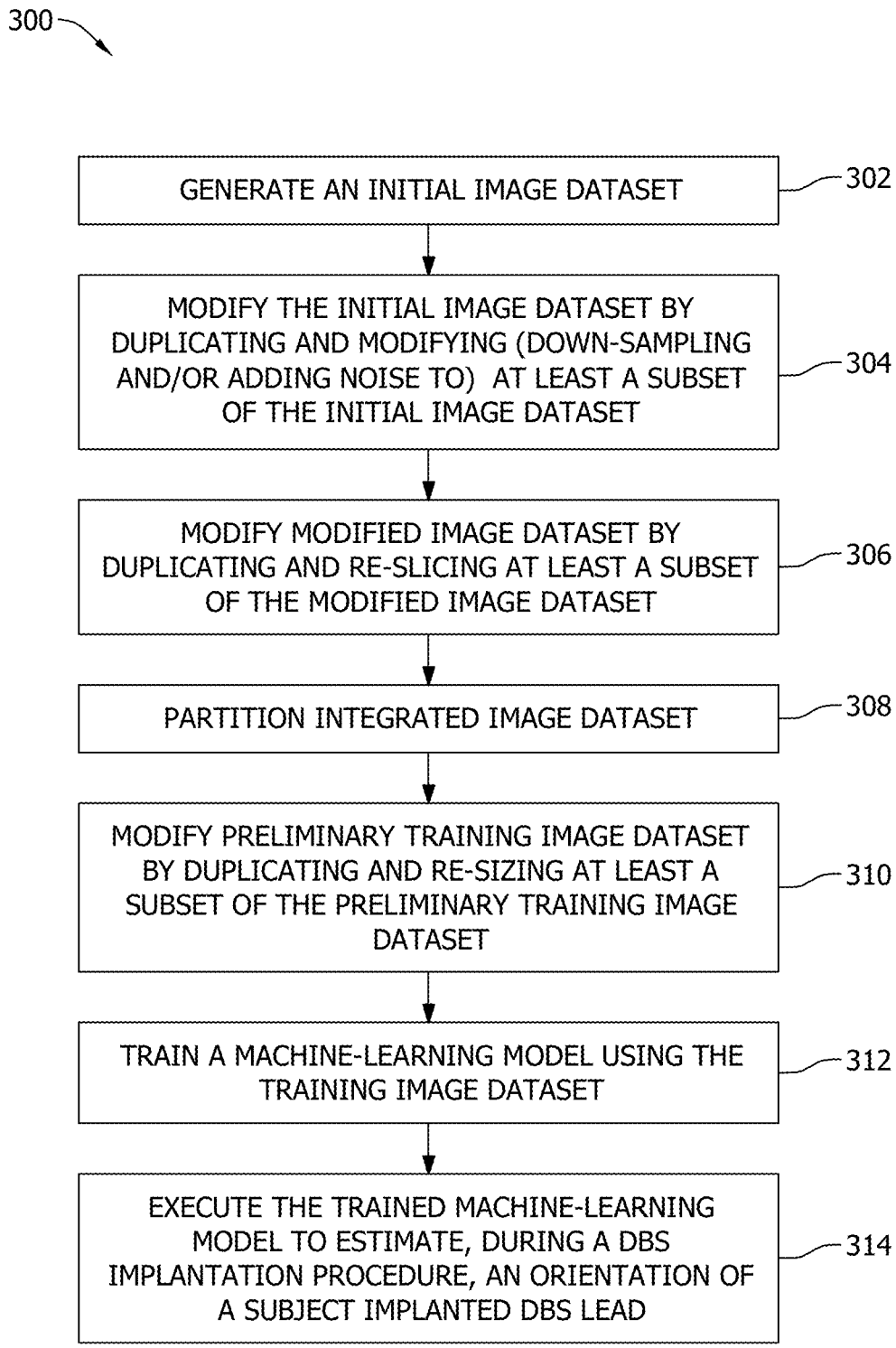
FIG. 3 is a flow diagram of a method of determining an orientation of a DBS lead.
Figure 7:
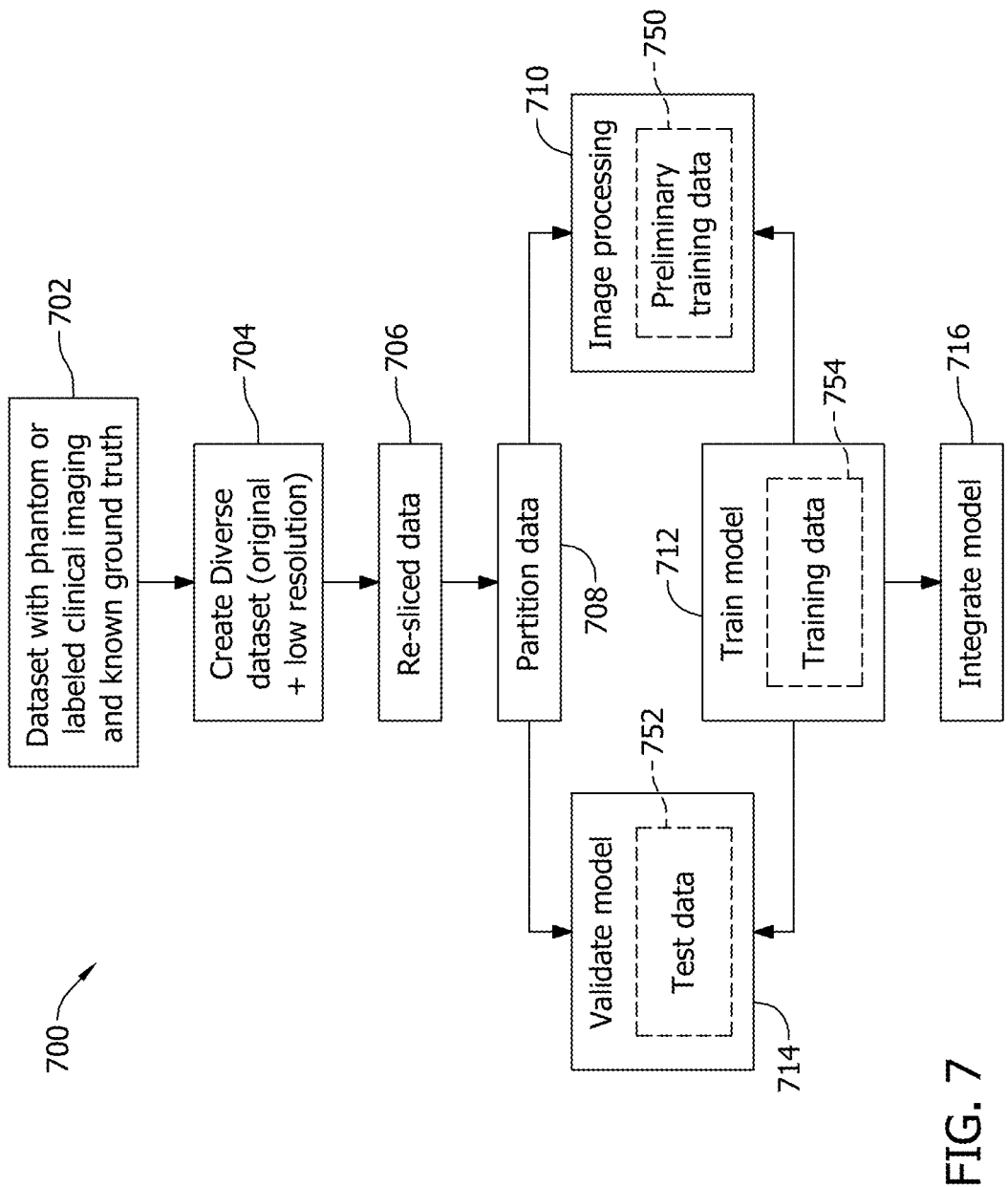
FIG. 7 is a flow diagram of a processor for predicting the rotational orientation of an implanted DBS lead.

In the illustrated embodiment, memory device 210 is one or more devices that enable information such as executable instructions (e.g., instructions for performing method 300 and/or process 700, shown in FIGS. 3 and 7, respectively) and/or other data to be stored and retrieved. Memory device 210 may include one or more (non-transitory) computer readable media, such as, without limitation, dynamic random access memory (DRAM), read-only memory (ROM), electrically erasable programmable read-only memory (EEPROM), static random access memory (SRAM), a solid state disk, and/or a hard disk. Memory device 210 may be configured to store, without limitation, application source code, application object code, source code portions of interest, object code portions of interest, configuration data, execution events and/or any other type of data.

In one exemplary embodiment, computing device 200 further includes at least one media output component 220 for presenting information to user 205. Media output component 220 may, for example, be any component capable of converting and conveying electronic information to user 205. In some embodiments, media output component 220 includes an output adapter (not shown), such as a video adapter or an audio adapter, which is operatively coupled to processor 215 and operatively couplable to an output device (also not shown), such as a display device (e.g., a cathode ray tube (CRT), liquid crystal display (LCD), light emitting diode (LED) display, or "electronic ink" display) or an audio output device (e.g., a speaker or headphones). In some embodiments, media output component 220 is configured to include and present a graphical user interface such as a web browser or a clinical programming application, to user 205.

In some embodiments, computing device 200 includes an input device 225 for receiving input from user 205. User 205 may use input device 225, without limitation, to provide commands for operating computing device 200 and/or provide commands for operating one or more remote devices (e.g., an imaging device) communicatively coupled to computing device 200. Input device 225 may include, for example, a keyboard, a pointing device, a mouse, a stylus, a touch sensitive panel (e.g., a touch pad or a touch screen), and the like. A single component such as a touch screen may function as both an output device of media output component 220 and input device 225.

Computing device 200, in the illustrated embodiment, includes a communication interface 230 coupled to processor 215. Communication interface 230 communicates with one or more remote devices, such as a clinician or patient programmer, an imaging device, controller device 160 (shown in FIG. 1), an external pulse generator, and the like. To communicate with remote devices, communication interface 230 may include, for example, a wired network adapter, a wireless network adapter, a radio-frequency (RF) adapter, and/or a mobile telecommunications adapter.

FIG. 3 is a flow diagram of a method 300 of estimating an orientation of an implanted DBS lead. Method 300 may be implemented, for example, by computing device 200 (shown in FIG. 2). Method 300 includes generating 302 an initial image dataset from a plurality of clinical images and a plurality of phantom images, each image in the initial image dataset including a depiction of an implanted DBS lead and a label of an orientation of the implanted DBS lead. As described herein, the plurality of clinical images in the initial image dataset may include at least one of intra-operative or post-operative CT images. The plurality of clinical images in the initial image dataset may further include at least one of intra-operative fluoroscopy images or post-operative fluoroscopy images. The initial image dataset may further include pre-operative MRI images identifying anatomical features of a brain in which the DBS lead is to be implanted. Generating 302 the initial image dataset may include, for example, generating 302 the initial image dataset from received clinical and/or phantom images.

Method 300 also includes modifying 304 the initial image dataset by duplicating and modifying at least a subset of the initial image dataset, to generate a modified image dataset. In some embodiments, therefore, modifying 304 may be alternatively referred to as expanding the initial image dataset and/or generating a modified image dataset. Modifying 304 includes at least one of down-sampling a respective image or adding noise to a respective image of the subset of the initial image dataset.

Method 300 further includes modifying 306 the modified image dataset by duplicating and re-slicing at least a subset of the modified image dataset, to generate an integrated image dataset. In some embodiments, therefore, modifying 306 may be alternatively referred to as expanding the initial and/or modified image dataset and/or generating in integrated image dataset. The re-slicing of modifying 306 includes re-slicing a respective image (e.g., an original image having an original primary imaging axis) along an alternative primary imaging axis.

Method 300 includes partitioning 308 the integrated image dataset into a preliminary training image dataset and a testing image dataset, and modifying 310 the preliminary training image dataset by duplicating and re-sizing at least a subset of the preliminary training image dataset with a localized field of view around the respective depiction of the implanted DBS lead, to generate a training image dataset. In some embodiments, modifying 310 may be alternatively referred to as expanding the preliminary training image dataset and/or generating the training image dataset.

Method 300 still further includes training 312 a machine-learning model using the training image dataset. Training 312 includes training the machine-learning model to associate one or more image artifacts with the orientation of the implanted DBS lead. Method 300 also includes executing 314 the trained machine-learning model to estimate, during a DBS implantation procedure, an orientation of a subject implanted DBS lead.

It should be readily understood that method 300 may include additional and/or alternative steps to those set forth above. For example, in some embodiments, method 300 may further include testing the trained machine-learning model using at least a subset of the testing image dataset. In some such embodiments, method 300 further includes refining the trained machine-learning model based on an outcome of the testing of the trained machine-learning model and, in some embodiments, validating the refined trained machine-learning model using at least another subset of the testing image dataset.

In some embodiments, method 300 includes (e.g., as part of executing 314) receiving, during the DBS implantation procedure, a subject image including a depiction of the subject implanted DBS lead with an unknown orientation, inputting the subject image to the trained machine-learning model; receiving, as output in response to the executing of the trained machine-learning model, the estimated orientation of the subject implanted DBS lead, and/or outputting, to a user of the computing device, the estimated orientation of the subject implanted DBS lead.

Figure 4B:
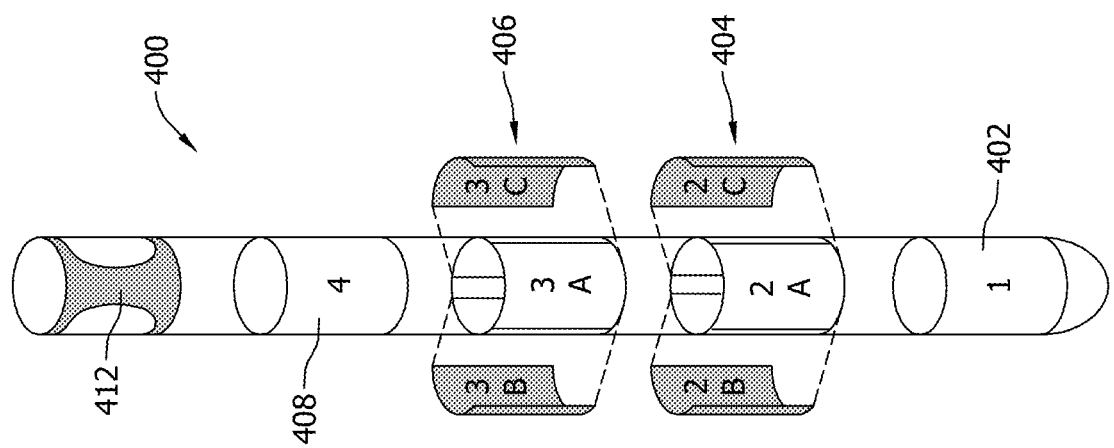
FIGS. 4A and 4B depict one embodiment of a DBS lead.
Figure 4A:
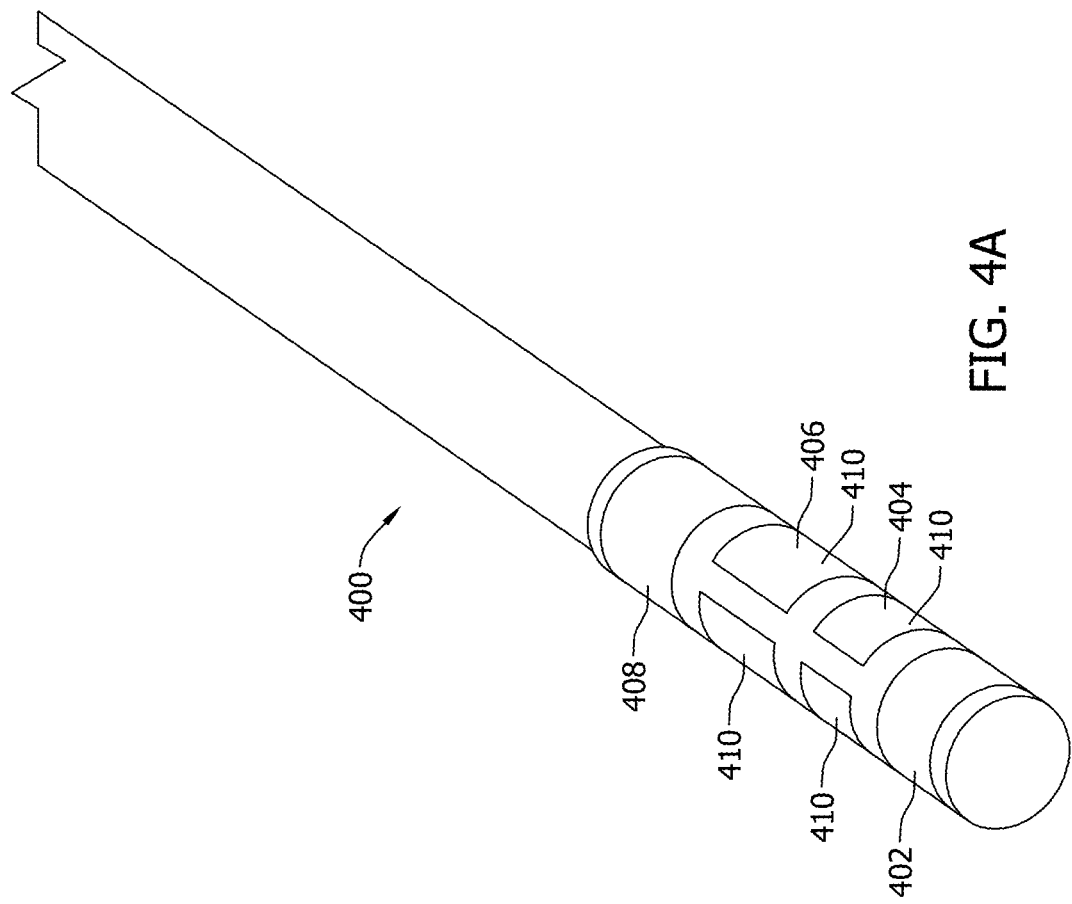

FIGS. 4A and 4B depict a DBS lead 400 that may be used in association with the systems and methods described herein. DBS lead 400 includes a first electrode 402, a second electrode 404, a third electrode 406, and a fourth electrode 408. In this embodiment, first electrode 402 and fourth electrode 408 are both ring electrodes. Further, second electrode 404 includes three segmented electrodes 410, illustrated in the exploded view of FIG. 4B. Likewise, third electrode 406 includes three segmented electrodes 410, illustrated in the exploded view of FIG. 4B. In FIG. 4B, first electrode 402 is designated "1", the three segmented electrodes 410 of second electrode 404 are designated "2A-2C", the three segmented electrodes 410 of third electrode 406 are designated "3A-3C", and fourth electrode 408 is designated "4". Those of skill in the art will appreciate that DBS lead 400 may have any suitable electrode configuration, and that the electrode configuration shown in FIGS. 4A and 4B is merely an example. Notably, however, an electrode configuration with rotationally asymmetric (e.g., having an odd number of segmented electrodes forming, for example, second electrode 404 and third electrode 406) is desirable for improving determinability of the orientation of the DBS lead 400 and, therefore, improving predictability of therapeutic application of stimulation using DBS lead 400.

In addition, DBS lead 400 includes an orientation marker 412, depicted in FIG. 4B with an "hourglass" shape. Orientation marker 412 is a radiopaque marker configured to identify an orientation of DBS lead 400. Specifically, orientation marker 412 is circumferentially aligned with the 2A and 3A segmented electrodes 410. Accordingly, where the direction or location of orientation marker 412 can be identified, the rotational orientation of DBS lead 400 can be readily estimated. For example, FIGS. 5A-5C depict representations of fluoroscopic images of an example DBS lead. These images readily reveal the relative rotational orientation of the orientation marker (e.g., similar to orientation marker 412) at 0°, 45°, and 90°, respectively.

Figure 6A:
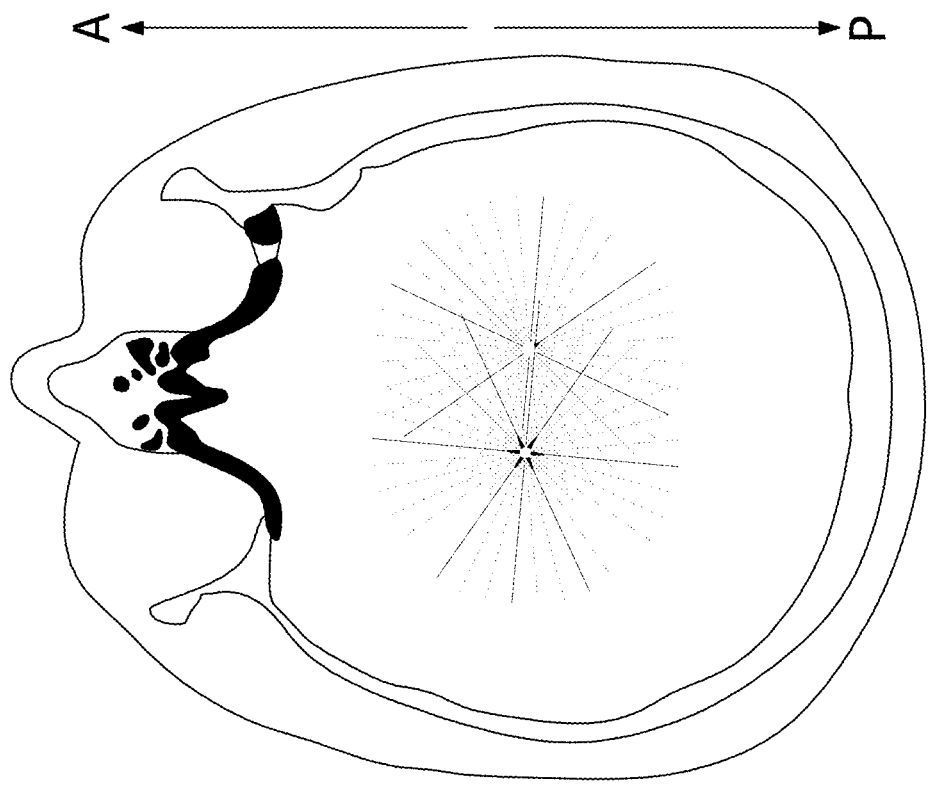
FIGS. 6A and 6B depict representations of CT images identifying a depth of an implanted DBS lead.
Figure 6B:
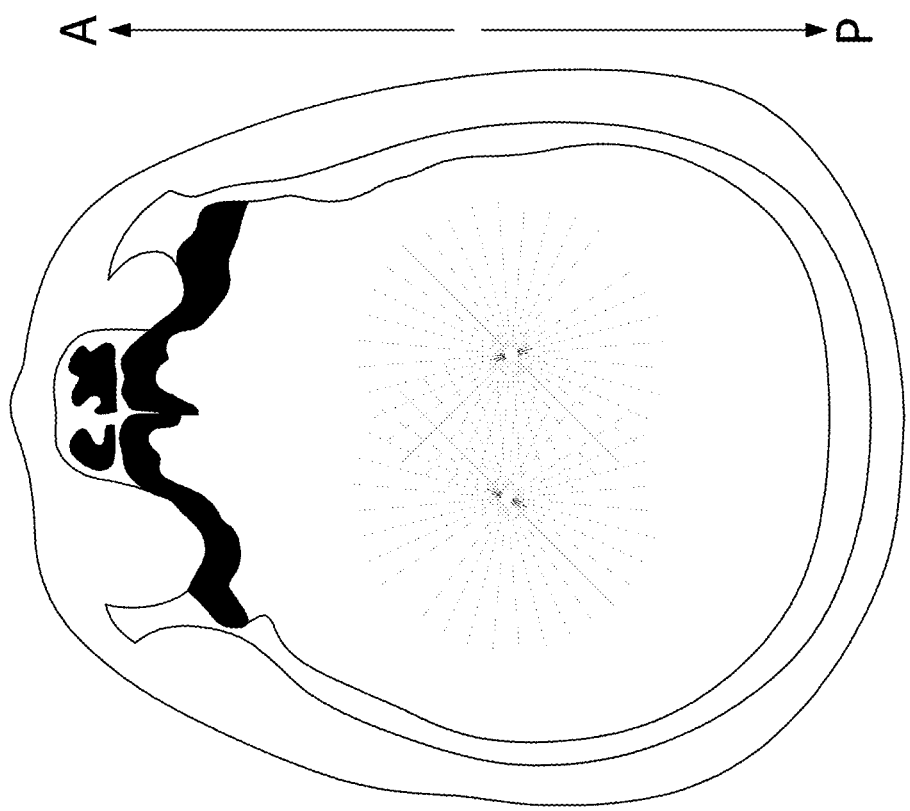

Notably, as described above herein, fluoroscopic images do not convey depth information, and therefore CT imaging is performed intra- and/or post-operatively to locate the DBS lead. However, the orientation of an orientation marker, such as orientation marker 412, cannot be readily identified in clinical-level CT imaging. For example, as shown in the representations of CT images depicted in FIGS. 6A and 6B, CT imaging may reveal useful imaging artifacts. In particular, FIG. 6A depicts a representation of a CT image with artifacts from the orientation marker of an example DBS lead. However, in FIG. 6A, to the naked human eye, the orientation of the lead could be either diagonally anterior or diagonally posterior, with some level of variance in either such direction. The particular orientation of DBS lead cannot be discerned. As another example, FIG. 6B depicts a representation of a CT image with artifacts from the segmented electrodes of such a DBS lead, which are rotationally asymmetric. Moreover, these artifacts of the segments electrodes are also laterally asymmetric (e.g., the left-hand artifacts are different from the right-hand artifacts) due to different lead trajectories, which is typical of DBS implantation procedures. Although the combination of these images (e.g., depictions of orientation marker artifacts and depictions of electrode artifacts) enable estimation of the DBS lead orientation, there remains ambiguity in these determinations due to the geometry of the orientation marker and the placement of the segmented electrodes. Accordingly, as set forth herein, a single imaging method does not accurately convey sufficient information to both locate the implanted DBS lead, and identify and validate its orientation.

Turning to FIG. 7, a flow diagram of a process 700 for predicting the rotational orientation of an implanted DBS lead is depicted. In one exemplary embodiment, one or more steps of process 700 are implemented by a computing device, such as computing device 200 (shown in FIG. 2). Execution of process 700 enables extracting information (otherwise unavailable or undiscernible by the human naked eye) from a single input image (e.g., a clinical-level CT image) to classify the information and detect and/or estimate the orientation of the implanted DBS lead. In particular, an image dataset is used to train and test a machine learning model to classify image features or artifacts that can be readily correlated to (e.g., are indicative of) the orientation of the DBS lead (e.g., of the orientation marker of the DBS lead). Process 700 may be similar to method 300, set forth above.

Process 700 includes generating 702 an initial image dataset. The initial image dataset includes a plurality of labelled training images of one or more imaging types. Each of the labelled images includes labels of the location and orientation of an implanted DBS lead depicts in the respective image. In the exemplary embodiment, the initial image dataset includes at least CT images depicting implanted DBS leads, the CT images captured intra-operatively and/or post-operatively. It is recognized that intra-operative CT images tend to have more noise than post-operative CT images; however, as described further herein, varying image qualities and resolutions are desirable for training the machine learning model. In some embodiments, the initial image dataset additionally includes fluoroscopic images, captured intra-operatively and/or post-operatively.

In some embodiments, the initial image dataset additionally includes phantom images labelled with ground truth data of the implanted DBS lead. Phantom images depict a biophysical representation or model of a patient with a DBS lead implanted in a representation of brain tissue. The biophysical model has similar properties to a human patient and real brain tissue. Notably, the biophysical model offers significant control over various procedural characteristics, such as relatively exact location and orientation of the implanted DBS lead, as well as imaging characteristics, such as quality and resolution. Accordingly, the ground truth is readily identified and provided in labelled phantom images.

Various types of phantom images may be included, such as fluoroscopic phantom images, CT phantom images, and MRI phantom images.

In some embodiments, the initial image dataset additionally includes MRI images, captured pre-operatively. Notably, such images do not include a label of an implanted DBS lead, because no such lead has yet been implanted when the MRI images are captured. However, MRI images depict anatomical details not available in other imaging types. Anatomical information can have significant effects in terms of DBS therapy. Specifically, activating different regions of the target tissue may have differential effects on the actual clinical outcome. Where MRI images are included in the initial image dataset, the MRI images are labelled to identify one or more anatomical details of tissue associated with an implantation location (i.e., where the DBS lead is eventually implanted). Accordingly, where these MRI images are included and are associated with corresponding intra-/post-operative CT and/or fluoroscopic images for the same patient, anatomical details at the implantation location can be accounted for in the machine learning model trained on such MRI images.

Therefore, the initial image dataset includes original images that are received from one or more sources, including clinical images received from physicians as well as phantom images received from, for example, model testing sources. In the exemplary embodiment, the initial image dataset includes the plurality of images having various image qualities and/or resolution. In particular, at least a subset of the images represents clinical-level image quality and/or resolution. Other subsets of the images represent greater image quality and/or resolution (e.g., phantom images).

Process 700 further includes generating 704 a modified, expanded image dataset using the initial image dataset. More specifically, at least a subset of the images in the initial dataset (e.g., original images) are duplicated and modified or augmented. Some of the plurality of images in the initial dataset are down-sampled, blurred, or have noise artificially added thereto, in order to generate additional training images with varying image resolutions and image qualities, respectively. By adding these uncertainties and variability into the training image set, the machine-learning model trained on the training image set will be capable of accurately interpreting a wider variety of input images, including low-quality clinical image data (e.g., intra-operative CT images), improving the generalizability of the machine-learning model when implemented in a clinical setting (e.g., during an implantation procedure).

Process 700 includes "re-slicing" or re-orienting 706 the modified image dataset. More specifically, at least a subset of the images in the initial and/or modified dataset are "re-sliced." Re-slicing, or re-orienting, in the context of the present disclosure refers to modifying a primary imaging axis of an original (or modified) image. For example, in typical clinical CT imaging, a primary imaging axis, or z-axis, is taken as the longitudinal axis of the patient (e.g., parallel to a direction from head to foot). To re-slice an image, the primary imaging axis is changed to an alternative primary imaging axis—that is, a primary imaging axis other than the conventional z-axis defined above. The tilt or trajectory of the implanted DBS lead can vary; the longitudinal axis of the implanted DBS lead is not always aligned with the conventional z-axis. At least some of the images (e.g., the phantom images) are re-sliced or re-oriented such that the known axis of the DBS lead is the modified, alternative primary imaging axis, which enables the machine learning model trained on such image data to identify image features associated with the tilt or trajectory of the DBS lead. It is contemplated that original images (e.g., unmodified images from the initial image dataset) and/or modified images may be re-sliced during step 706. The plurality of images from steps 702, 704, and 706 are collectively referred to as an integrated image dataset. That is, the integrated image dataset includes original images, modified (e.g., down-sampled and/or noisy) images, and re-sliced images.

Process 700 further includes partitioning 708 the integrated image dataset into a preliminary training image dataset (e.g., preliminary training data 750) and a test image dataset (e.g., test data 752). Partitioning 708 is a pseudo-random process step in that the process of dividing images between preliminary training data 750 and test data 752 is random but a representational portion of the integrated image dataset must be included in test data 752, including a representation portion of images of each imaging type, varying image quality, varying image resolution, and re-sliced image data. Test data 752 may represent a relatively small portion of the integrated image dataset, such as 10-30% of the integrated image dataset.

Once the integrated image dataset is partitioned 708, image processing is performed on preliminary training data 750, represented at step 710. During image processing 710, at least a subset of the images included in preliminary training data 750 are duplicated and re-sized to focus or localize the field of view on the implanted DBS lead depicted in the respective image. Thereby, image artifacts unrelated to the location and/or orientation of the DBS lead may be effectively ignored, for these re-sized images. Moreover, this resizing, focused specifically on fields of view of interest, improves the signal-to-noise ratio for these re-sized images, relative to their non-re-sized counterpart images. The image dataset including preliminary training data 750 and the re-sized images is collectively referred to as a training image dataset (e.g., training data 754).

Training data 754 is input to a machine learning model to train 712 the machine learning model, also referred to herein as a machine learning algorithm. Training 712 includes training the machine learning algorithm to associate particular image artifacts or features with the labelled location and/or orientation of the implanted DBS lead. For example, where an image (e.g., a CT image) depicts a "slice" of the implanted DBS lead corresponding to the orientation marker, image artifacts reflect two potential rotational orientations of the implanted DBS lead, with some amount of variance. As another example, where an image (e.g., a CT image) depicts a "slice" of the implanted DBS lead corresponding to one of the segmented electrodes (e.g., the second or third electrode, in the embodiment of a DBS lead shown in FIGS. 4A and 4B), the rotational asymmetry of the electrodes is represented, but (to the human naked eye) it cannot be determined which electrode (e.g., 2A, 2B, 2C) is facing in any direction.

During training 712, the machine learning algorithm uses the image labels to identify features of the images (unrecognized by the human naked eye) that more precisely estimate the actual orientation of the DBS lead at any "slice" or imaging depth. The machine learning model is also trained 712 to identify those image features or artifacts that are more (or most) indicative of DBS lead orientation and/or location. Such image features or artifacts may include, for example and without limitation, features related to intensity, shade, gradient, spatial frequency (e.g., information from the k-space before image reconstruction), including relative and/or absolute values thereof, and/or relational features. Image features or artifacts may be classified based on their relative indicative effect. Those features that are classified as relatively more indicative may weighed more heavily in generating the output from the machine learning model— that is, the estimation of the orientation and/or the location of the implanted DBS lead depicted in an input subject image. The variability in at least one of the imaging type, image quality, image resolution, image orientation, and/or image field of view of training data 754 improves the estimating capability of the trained machine learning model.

In some embodiments, where MRI imaging data is available in training data 754, training 712 also includes training the machine learning model to associate particular image artifacts representing anatomical features with the labelled location and/or orientation of the implanted DBS lead in related CT and/or fluoroscopic images.

In some embodiments, the machine learning model, or machine learning model, is an artificial neural network model (e.g., a convolutional neural network model) trained 712 used transfer learning techniques. The transfer learning techniques enable the "transfer" of relationship learned using high-quality image data (e.g., phantom data with labelled ground truth) to lower-quality image data (e.g., clinical data). These techniques accelerate the training process and also improve the generalizability and estimating capability of the trained machine learning model. It should be readily understood that additional and/or alternative models and/or techniques may be applied during training 712, such as, but not limited to Deep Neural Networks (DNN), Random forest (RF), K-nearest neighbor (KNN), support vector machine (SVM), logistic regression, ensemble learning, and multi-layer perception (MLP). The specific models used may depend on the particular training data 754 (e.g., the combination of image types) used to train 712 the algorithm.

The trained machine learning model is configured to receive, as input thereto, a subject image including a depiction of a subject implanted DBS lead with an unknown orientation and/or an unknown location. The trained machine learning model is configured to generate, as output therefrom an estimation of the orientation and/or location of the subject implanted DBS lead depicted in the subject image.

Once the machine learning model is trained 712, a model validation step 714 is implemented to test or validate the trained machine learning model. Test data 752 is used as input to the trained machine learning model, and the output from the trained machine learning model is reviewed to determine whether the output estimations match the labelled (known) orientation and/or location of the DBS lead depicted in images of test data 752. If necessary, based on the outcome of testing 714, the trained machine learning model is refined or adjusted to ensure accurate output estimations. Where available in test data 752, phantom images with ground truth labels may be used for a final test or validated of the trained machine learning model, because the output from the model can be precisely compared to the ground truth labels.

After the trained machine learning model has been fully tested and/or validated 714, the trained machine learning model is integrated 716 into a clinical application for use in a clinical setting (e.g., during an implantation procedure). The application may be implemented by the same computing device programmed to implement process 700. Alternatively, the clinical application may be implemented by one or more other computing devices.

In operation, as described above, a subject image, such as in intra-operative CT image, is input to the trained machine learning model. The subject image depicts an implanted DBS lead for which the orientation and/or location is unknown (e.g., to the operating physician). The trained machine learning model processed the subject image and outputs an estimation of the orientation and/or the location of the implanted DBS lead.

In some embodiments, the estimation is overlaid on at least a portion of the subject image, such as an icon, one or more words or numbers, and the like, overlaid on and/or adjacent to the depicted DBS lead. In other embodiments, the estimation is output in an alternative format. The estimation may be output on a user interface of a computing device (e.g., computing device 200), such as a screen visible to the operating physician. Additionally or alternatively, the estimation may be output in a physical format (e.g., as a printed image or message). The estimation enables reducing or eliminating the conventional "trial and error" procedures for locating the DBS lead. Based on the estimation, the operating physician may adjust the location and/or orientation of the DBS lead in response to the estimation. This process can be iterated until the desired orientation and/or location of the DBS lead is achieved, at which point the operating physician may, in some instances, initiate stimulation therapy using the DBS lead.

In one exemplary implementation, the trained machine learning model is integrated into an application executed on a computing device (e.g., computing device 200) with a graphical user interface. The computing device is communicatively coupled to an imaging device (e.g., a CT imaging device) configured to intra-operatively capture the subject image depicting the implanted DBS lead. Once the subject image is captured, the computing device is configured to execute the trained machine learning model (e.g., automatically, in response to detecting a subject image has been captured by the imaging device and/or received at the computing device, and/or in response to a command). The computing device also displays the captured subject image on the graphical user interface. The trained machine learning model generates the output—the estimation—and displays the estimation as an overlay on the captured subject image, conveying (through icons, animations, words, numbers, etc.) to the operating physician the estimated orientation and/or location of the implanted DBS lead.

The present disclosure provides systems and methods for estimating an orientation and/or location of a DBS lead, which can be implemented in a clinical setting (e.g., during a DBS lead implantation procedure). In particular, an initial image dataset is generated from a plurality of clinical images and a plurality of phantom images, each image in the initial image dataset including a depiction of an implanted DBS lead and a label of an orientation of the implanted DBS lead; the initial image dataset is modified by duplicating and modifying at least a subset of the initial image dataset, the modifying including at least one of down-sampling a respective image or adding noise to a respective image of the subset of the initial image dataset, to generate a modified image dataset; the modified image dataset is further modified by duplicating and re-slicing at least a subset of the modified image dataset, the re-slicing including re-slicing a respective image along an alternative primary imaging axis, to generate an integrated image dataset; the integrated image dataset is partitioned into a preliminary training image dataset and a testing image dataset; the preliminary training image dataset is modified by duplicating and re-sizing at least a subset of the preliminary training image dataset with a localized field of view around the respective depiction of the implanted DBS lead, to generate a training image dataset; a machine-learning model is trained using the training image dataset, including training the machine-learning model to associate one or more image artifacts with the orientation of the implanted DBS lead; and the trained machine-learning model is executed to estimate, during a DBS implantation procedure, an orientation of a subject implanted DBS lead.

In this way, an operating physician is informed of this orientation and/or location in substantially real-time. Therefore, the systems and methods of the present disclosure represent a significant improvement over conventional methods for determining the placement of an implanted DBS lead (e.g., via "trial-and-error").

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A computing device for estimating an orientation of an implanted deep brain stimulation (DBS) lead, the computing device comprising:
    a processor; and
    a memory device communicatively coupled to the processor, the memory device including instructions that, when executed, cause the processor to:
        generate an initial image dataset from a plurality of clinical images and a plurality of phantom images, each image in the initial image dataset including a depiction of an implanted DBS lead and a label of an orientation of the implanted DBS lead;
        modify the initial image dataset by duplicating and modifying at least a subset of the initial image dataset, the modifying including at least one of down-sampling a respective image or adding noise to a respective image of the subset of the initial image dataset, to generate a modified image dataset;
        modify the modified image dataset by duplicating and re-slicing at least a subset of the modified image dataset, the re-slicing including re-slicing a respective image along an alternative primary imaging axis, to generate an integrated image dataset;
        partition the integrated image dataset into a preliminary training image dataset and a testing image dataset;
        modify the preliminary training image dataset by duplicating and re-sizing at least a subset of the preliminary training image dataset with a localized field of view around the respective depiction of the implanted DBS lead, to generate a training image dataset;
        train a machine-learning model using the training image dataset, including training the machine-learning model to associate one or more image artifacts with the orientation of the implanted DBS lead; and
        execute the trained machine-learning model to estimate, during a DBS implantation procedure, an orientation of a subject implanted DBS lead.

2. The computing device of claim 1, wherein the machine-learning model is an artificial neural network, and wherein training the machine-learning model includes implementing transfer learning techniques.

3. The computing device of claim 1, wherein the plurality of clinical images in the initial image dataset includes at least one of intra-operative or post-operative computed tomography (CT) images.

4. The computing device of claim 3, wherein the plurality of clinical images in the initial image dataset further includes at least one of intra-operative fluoroscopy images or post-operative fluoroscopy images.

5. The computing device of claim 3, wherein the initial image dataset further includes pre-operative magnetic resonance imaging (MRI) images identifying anatomical features of a brain in which the DBS lead is to be implanted.

6. The computing device of claim 1, wherein the instructions further cause the processor to:
    test the trained machine-learning model using at least a subset of the testing image dataset.

7. The computing device of claim 6, wherein the instructions further cause the processor to:
    refine the trained machine-learning model based on an outcome of the testing of the trained machine-learning model.

8. The computing device of claim 7, wherein the instructions further cause the processor to:
    validate the refined trained machine-learning model using at least another subset of the testing image dataset.

9. The computing device of claim 1, wherein the instructions further cause the processor to:
    receive, during the DBS implantation procedure, a subject image including a depiction of the subject implanted DBS lead with an unknown orientation;
    input the subject image to the trained machine-learning model;
    receive, as output in response to the executing of the trained machine-learning model, the estimated orientation of the subject implanted DBS lead; and
    output, to a user of the computing device, the estimated orientation of the subject implanted DBS lead.

10. A computer-implemented method for estimating deep brain stimulation (DBS) lead orientation, the method comprising:
generating an initial image dataset from a plurality of clinical images and a plurality of phantom images, each image in the initial image dataset including a depiction of an implanted DBS lead and a label of an orientation of the implanted DBS lead;
modifying the initial image dataset by duplicating and modifying at least a subset of the initial image dataset, the modifying including at least one of down-sampling a respective image or adding noise to a respective image of the subset of the initial image dataset, to generate a modified image dataset;
modifying the modified image dataset by duplicating and re-slicing at least a subset of the modified image dataset, the re-slicing including re-slicing a respective image along an alternative primary imaging axis, to generate an integrated image dataset;
partitioning the integrated image dataset into a preliminary training image dataset and a testing image dataset;
modifying the preliminary training image dataset by duplicating and re-sizing at least a subset of the preliminary training image dataset with a localized field of view around the respective depiction of the implanted DBS lead, to generate a training image dataset;
training a machine-learning model using the training image dataset, including training the machine-learning model to associate one or more image artifacts with the orientation of the implanted DBS lead; and
executing the trained machine-learning model to estimate, during a DBS implantation procedure, an orientation of a subject implanted DBS lead.

11. The method of claim 10, wherein training the machine-learning model comprises training an artificial neural network by implementing transfer learning techniques.

12. The method of claim 10, wherein generating the initial image data set includes receiving the plurality of clinical images in the initial image dataset including at least one of intra-operative or post-operative computed tomography (CT) images.

13. The method of claim 12, wherein generating the initial image data set includes receiving the plurality of clinical images further including at least one of intra-operative fluoroscopy images or post-operative fluoroscopy images.

14. The method of claim 12, wherein generating the initial image data set includes receiving pre-operative magnetic resonance imaging (MRI) images identifying anatomical features of a brain in which the DBS lead is to be implanted.

15. The method of claim 10, further comprising:
testing the trained machine-learning model using at least a subset of the testing image dataset.

16. The method of claim 15, further comprising:
refining the trained machine-learning model based on an outcome of the testing of the trained machine-learning model.

17. The method of claim 16, further comprising:
validating the refined trained machine-learning model using at least another subset of the testing image dataset.

18. The method of claim 10, further comprising:
receiving, during the DBS implantation procedure, a subject image including a depiction of the subject implanted DBS lead with an unknown orientation;
inputting the subject image to the trained machine-learning model;
receiving, as output in response to the executing of the trained machine-learning model, the estimated orientation of the subject implanted DBS lead; and
outputting, to a user, the estimated orientation of the subject implanted DBS lead.

19. Non-transitory computer-readable media having computer-executable instructions thereon, wherein when executed by a processor of a computing device communicatively coupled to a memory device, cause the processor of the computing device to:
generate an initial image dataset from a plurality of clinical images and a plurality of phantom images, each image in the initial image dataset including a depiction of an implanted DBS lead and a label of an orientation of the implanted DBS lead;
modify the initial image dataset by duplicating and modifying at least a subset of the initial image dataset, the modifying including at least one of down-sampling a respective image or adding noise to a respective image of the subset of the initial image dataset, to generate a modified image dataset;
modify the modified image dataset by duplicating and re-slicing at least a subset of the modified image dataset, the re-slicing including re-slicing a respective image along an alternative primary imaging axis, to generate an integrated image dataset;
partition the integrated image dataset into a preliminary training image dataset and a testing image dataset;
modify the preliminary training image dataset by duplicating and re-sizing at least a subset of the preliminary training image dataset with a localized field of view around the respective depiction of the implanted DBS lead, to generate a training image dataset;
train a machine-learning model using the training image dataset, including training the machine-learning model to associate one or more image artifacts with the orientation of the implanted DBS lead; and
execute the trained machine-learning model to estimate, during a DBS implantation procedure, an orientation of a subject implanted DBS lead.

20. The non-transitory computer-readable media of claim 19, wherein the computer-executable instructions further cause the processor to:
test the trained machine-learning model using at least a subset of the testing image dataset.

21. The non-transitory computer-readable media of claim 20, wherein the computer-executable instructions further cause the processor to:
refine the trained machine-learning model based on an outcome of the testing of the trained machine-learning model; and
validate the refined trained machine-learning model using at least another subset of the testing image dataset.

* * * * *